United States Patent
Grass et al.

(10) Patent No.: US 11,257,262 B2
(45) Date of Patent: Feb. 22, 2022

(54) MODEL REGULARIZED MOTION COMPENSATED MEDICAL IMAGE RECONSTRUCTION

(71) Applicant: KONINKLIJKE PHILIPS N.V., Eindhoven (NL)

(72) Inventors: Michael Grass, Buchholz In der Nordheide (DE); Rolf Dieter Bippus, Hamburg (DE); Axel Thran, Hamburg (DE); Cristian Buerger, Hamburg (DE); Manindranath Vembar, Twinsburg, OH (US); Kevin Martin Brown, Chardon, OH (US)

(73) Assignee: KONINKLIJKE PHILIPS N.V., Eindhoven (NL)

(*) Notice: Subject to any disclaimer, the term of this patent is extended or adjusted under 35 U.S.C. 154(b) by 83 days.

(21) Appl. No.: 16/325,268

(22) PCT Filed: Aug. 22, 2017

(86) PCT No.: PCT/EP2017/071126
§ 371 (c)(1),
(2) Date: Feb. 13, 2019

(87) PCT Pub. No.: WO2018/037005
PCT Pub. Date: Mar. 1, 2018

(65) Prior Publication Data
US 2019/0188885 A1   Jun. 20, 2019

Related U.S. Application Data

(60) Provisional application No. 62/377,809, filed on Aug. 22, 2016.

(51) Int. Cl.
*G06T 11/00* (2006.01)
*A61B 6/03* (2006.01)
(Continued)

(52) U.S. Cl.
CPC ............ *G06T 11/008* (2013.01); *A61B 6/032* (2013.01); *A61B 6/486* (2013.01); *A61B 6/503* (2013.01);
(Continued)

(58) Field of Classification Search
CPC ......... A61B 6/032; A61B 6/486; A61B 6/503; A61B 6/5205; A61B 6/5235;
(Continued)

(56) References Cited

U.S. PATENT DOCUMENTS

| 8,184,883 B2 | 5/2012 | Grass |
| 8,326,086 B2 | 12/2012 | Carlsen |

(Continued)

FOREIGN PATENT DOCUMENTS

| WO | 2010/073147 | 7/2010 |
| WO | 2015/092612 | 6/2015 |
| WO | 2017/109662 | 6/2017 |

OTHER PUBLICATIONS

Stayman, et al.: "Model-Based Tomographic Reconstruction of Objects Containing Known Components", IEEE Transactions on Medical Imaging, vol. 31, No. 10, Oct. 2012.

*Primary Examiner* — Manuchehr Rahmjoo
(74) *Attorney, Agent, or Firm* — Larry Liberchuk (57) ABSTRACT

A medical imaging system (200) includes a masking unit (234), an image registration unit (238), a motion estimator (240) and a motion compensating reconstructor (244). The masking unit constructs a mask for each reconstructed volumetric phase image of a plurality of reconstructed volumetric phase images that masks portions of a corresponding image external to an anatomical model fitted to a segmented at least one anatomical structure, 5 wherein the plurality of reconstructed volumetric phase images include a target phase and a plurality of temporal neighboring phases
(Continued)

reconstructed from projection data. The image registration unit registers the masked reconstructed volumetric phase images. The motion estimator estimates motion between the target phase and the plurality of temporal neighboring phases according to the model based on the registered masked reconstructed 10 volumetric phase images. The motion compensating reconstructor reconstructs a motion compensated medical image from the projection data using the estimated motion of the registered masked reconstructed volumetric phase images.

20 Claims, 4 Drawing Sheets (51) Int. Cl.
 A61B 6/00 (2006.01)
 G06T 7/10 (2017.01)
 G06T 3/00 (2006.01)
 G06T 7/11 (2017.01)
 G06T 5/30 (2006.01)
 G06T 5/50 (2006.01)
 G06T 7/20 (2017.01)
(52) U.S. Cl.
 CPC .......... *A61B 6/5205* (2013.01); *A61B 6/5235* (2013.01); *A61B 6/5252* (2013.01); *A61B 6/5264* (2013.01); *A61B 6/541* (2013.01); *G06T 3/0068* (2013.01); *G06T 3/0081* (2013.01); *G06T 5/30* (2013.01); *G06T 5/50* (2013.01); *G06T 7/10* (2017.01); *G06T 7/11* (2017.01); *G06T 7/20* (2013.01); *G06T 11/006* (2013.01); *A61B 6/5288* (2013.01); *G06T 2207/10081* (2013.01); *G06T 2207/20024* (2013.01); *G06T 2207/30048* (2013.01); *G06T 2207/30061* (2013.01); *G06T 2207/30101* (2013.01)

(58) Field of Classification Search
 CPC ... A61B 6/5252; A61B 6/5264; A61B 6/5288; A61B 6/541; G06T 11/006; G06T 11/008; G06T 2207/10081; G06T 2207/20024; G06T 2207/30048; G06T 2207/30061; G06T 2207/30101; G06T 3/0068; G06T 3/0081; G06T 5/30; G06T 5/50; G06T 7/10; G06T 7/11; G06T 7/20; G06T 7/246
 See application file for complete search history.

(56) References Cited

U.S. PATENT DOCUMENTS

| | | | |
|---|---|---|---|
| 9,414,773 B2 | 8/2016 | Kabus | |
| 2008/0304744 A1 | 12/2008 | Peters | |
| 2009/0074278 A1 | 3/2009 | Beaulieu | |
| 2010/0111386 A1* | 5/2010 | El-Baz | G06T 7/33 382/128 |
| 2010/0183214 A1 | 7/2010 | Mccollough | |
| 2011/0038516 A1 | 2/2011 | Koehler | |
| 2012/0022367 A1* | 1/2012 | Wong | A61B 5/0075 600/427 |
| 2012/0201428 A1* | 8/2012 | Joshi | G06T 11/006 382/107 |
| 2012/0275673 A1* | 11/2012 | Star-Lack | G06T 11/005 382/131 |
| 2013/0070995 A1* | 3/2013 | Chou | G06T 7/344 382/131 |
| 2014/0270450 A1 | 9/2014 | Grass | |
| 2016/0104279 A1* | 4/2016 | Li | G06K 9/52 382/131 |
| 2016/0163095 A1 | 6/2016 | Wollenweber | |
| 2016/0302757 A1* | 10/2016 | Pizaine | A61B 6/461 |

\* cited by examiner

MODEL REGULARIZED MOTION COMPENSATED MEDICAL IMAGE RECONSTRUCTION

CROSS REFERENCE TO RELATED APPLICATIONS

This application is the U.S. National Phase application under 35 U.S.C. § 371 of International Application No. PCT/EP2017/071126 filed Aug. 22, 2017, published as WO 2018/037005 on Mar. 1, 2018, which claims the benefit of U.S. Provisional Patent Application No. 62/377,809 filed Aug. 22, 2016. These applications are hereby incorporated by reference herein.

FIELD OF THE INVENTION

The following generally relates to medical imaging and more specifically to motion compensated computed tomography (CT) reconstruction, and is also amenable to other types of imaging modalities, such as positron emission tomography (PET), single photon emission computed tomography (SPECT), magnetic resonance (MR), C-arm CT, and combinations thereof.

BACKGROUND OF THE INVENTION

Motion compensated reconstruction seeks to remove motion artifacts in reconstructed images, such as blurring and streaks. Motion artifacts are typically removed by compensating for periodic motion, such as cardiac motion and/or respiratory motion, in the subject during image reconstruction, and can compensate for types of involuntary motion. Motion compensated CT reconstruction, for example, can be used in non-invasive coronary angiography to quantify coronary artery disease. In such an example, the imaging procedure is directed to an image without motion artifacts with a minimum of X-ray radiation exposure, such as can be captured within a single rotation, that is 240° or greater, of a radiation source around the subject. The rotation provides sufficient projection data for a volumetric reconstruction. However, the projection data acquired within the single rotation includes motion.

Projection data is acquired using prospectively and/or respectively gated acquisition that typically include the use of one or more motion monitors, such as an electrocardiography (ECG) monitor, respiratory monitor and the like. The monitors typically include wire leads from sensing elements, such as electrodes, that connect the sensing elements and carry a signal to the monitoring device. Typical approaches to motion compensated reconstruction use elastic registration between the entire volumes of each reconstructed multi-phase image. That is, motion vectors are computed based on the elastic movement of the entire imaged volume present in each phase image.

Figure 1A:
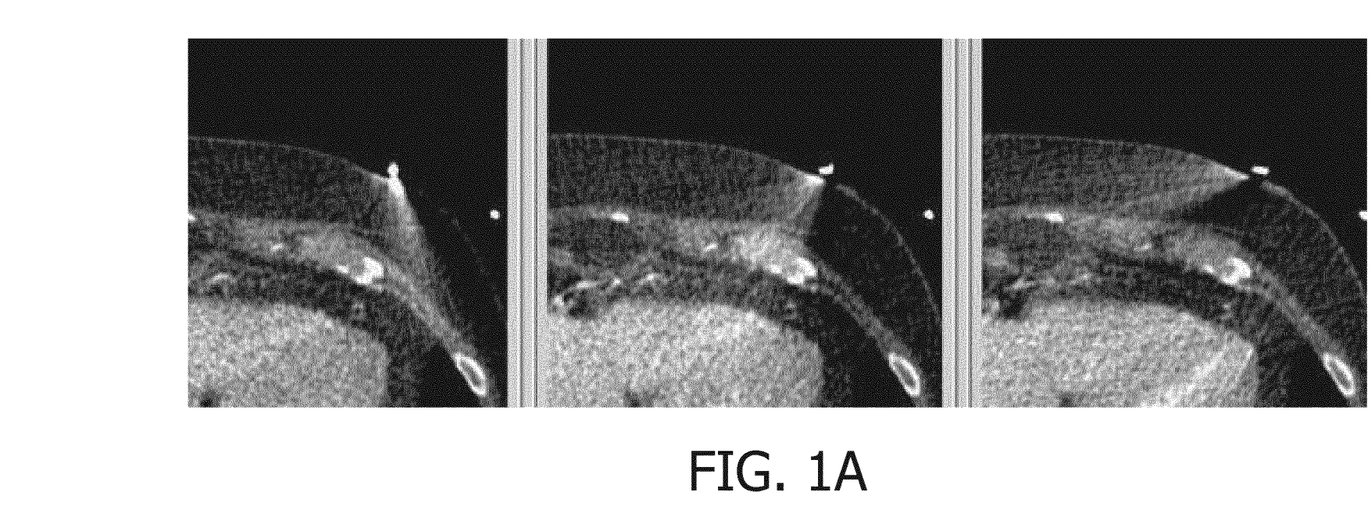
FIG. 1A illustrates examples of a two dimensional view of reconstructed cardiac CT images at different rotational positions of an imaging radiation source about a subject, which include artifacts from an electrode.
Figure 1B:
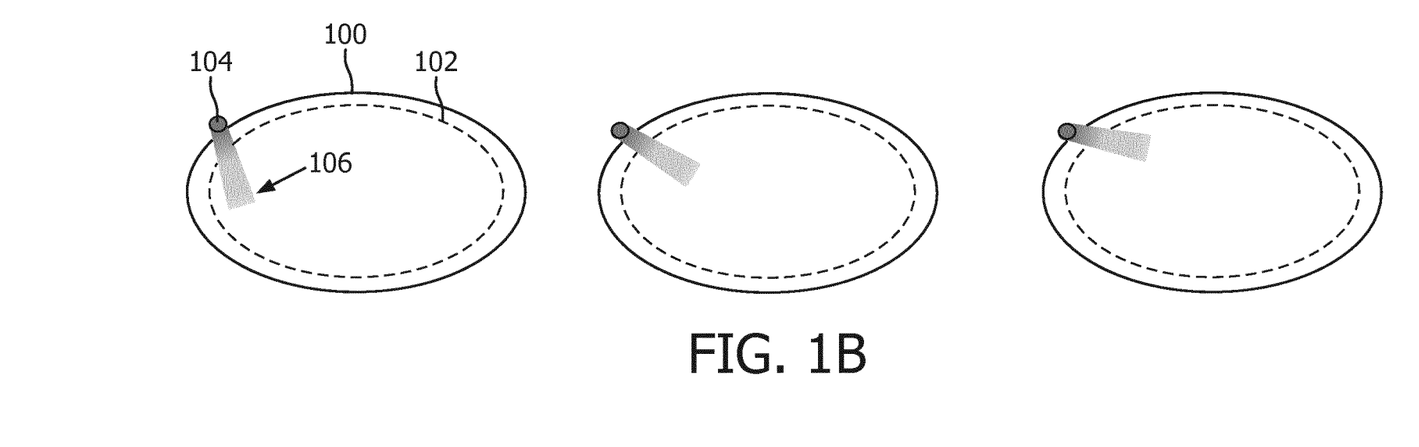

FIG. 1A shows three cardiac CT images of the same subject with streak artifacts, which are not due to motion of organ, rather due to a presence of an electrode on the patient and angular positions of the radiation source about the subject relative to the electrode. In a first image (from left to right), the streaks emanate from a point of high intensity of the electrode and fan toward a 5 o'clock orientation. In a second image, the streaks fan toward a 7 o'clock orientation, and in a third image, the streaks fan toward a 9 o'clock position. The change in position of streaks in the images mimic an appearance of motion that changes the computed motion vectors in the elastic registration between the volumes of the multi-phase images. FIG. 1B illustrates the same concept diagrammatically across three images. Each diagrammed image includes a portion of a subject, such as a cross section of a torso 100 with a visceral cavity 102, and each image includes a metal object 104 exterior to the surface of the torso 100 and streak artifacts 106. The streak artifacts 106 in each image extend inside the surface of the torso and are generated by varying angular range reconstruction.

SUMMARY OF THE INVENTION

Aspects described herein address the above-referenced problems and others.

The following describes model regularized motion compensated reconstruction. Motion phase images are reconstructed from projection data. Anatomical structures in the motion phase images are segmented using fitted anatomical models, such as a heart model and/or lung model. Volumetric masks are constructed for each phase image, which masks portions of each phase image external to the fitted anatomical models and/or anatomical structures in a registration. In some embodiments the mask is dilated to include a predetermined distance external to the fitted model. Motion is estimated from the registered masked phase images. A motion compensated image is reconstructed from the projection data compensating for the estimated motion. A filter can be used to enhance vascular structures.

The following is described in terms of a CT system for the sake of brevity. However, the methods and system are amenable to other medical imaging modalities, such as PET, SPECT, MR, C-arm CT, and combinations thereof.

In one aspect, a medical imaging system includes a masking unit, an image registration unit, a motion estimator and a motion compensating reconstructor. The masking unit constructs a mask for each reconstructed volumetric phase image of a plurality of reconstructed volumetric phase images that masks portions of a corresponding image external to an anatomical model fitted to a segmented at least one anatomical structure, wherein the plurality of reconstructed volumetric phase images include a target phase and a plurality of temporal neighboring phases reconstructed from projection data. The image registration unit registers the masked reconstructed volumetric phase images. The motion estimator estimates motion between the target phase and the plurality of temporal neighboring phases according to the model based on the registered masked reconstructed volumetric phase images. The motion compensating reconstructor reconstructs a motion compensated medical image from the projection data using the estimated motion of the registered masked reconstructed volumetric phase images.

In another aspect, a method of motion compensated medical image reconstruction includes constructing a mask for each reconstructed volumetric phase image of a plurality of reconstructed volumetric phase images that masks portions of a corresponding image external to an anatomical model fitted to a segmented at least one anatomical structure, wherein the plurality of reconstructed volumetric phase images include a target phase and a plurality of temporal neighboring phases reconstructed from projection data. The masked reconstructed volumetric phase images are registered. Motion between the target phase and the plurality of temporal neighboring phases is estimated according to the model based on the registered masked reconstructed volumetric phase images. A motion compensated medical image is reconstructed from the projection data using the estimated motion of the registered masked reconstructed volumetric phase images.

In another aspect, a method of motion compensated computed tomography (CT) reconstruction includes reconstructing volumetric phase images at a target phase and a plurality of temporal neighboring phases of at least one anatomical structure of a subject from CT projection data. The at least one anatomical structure is segmented in each of the reconstructed volumetric phase images using a model based segmentation that fits the model to the at least one anatomical structure. A mask is constructed for each reconstructed volumetric phase image that masks portions of the corresponding image external a predetermined distance to the surface of the fitted model. Each masked reconstructed volumetric phase image is filtered, which enhances vascular structures in the non-masked regions. The masked reconstructed volumetric phase images are elastically registered. Motion is estimated between the target phase and the plurality of temporal neighboring phases according to the fitted model based on the elastically registered masked reconstructed volumetric phase images. A motion compensated CT image is reconstructed at the target phase from the CT projection data using the estimated motion of the elastically registered masked reconstructed volumetric phase images.

These and other aspects of the invention will be apparent from and elucidated with reference to the embodiment(s) described hereinafter.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

FIG. 1B diagrammatically illustrates examples of a two dimensional view of

DETAILED DESCRIPTION OF EMBODIMENTS

Figure 2:
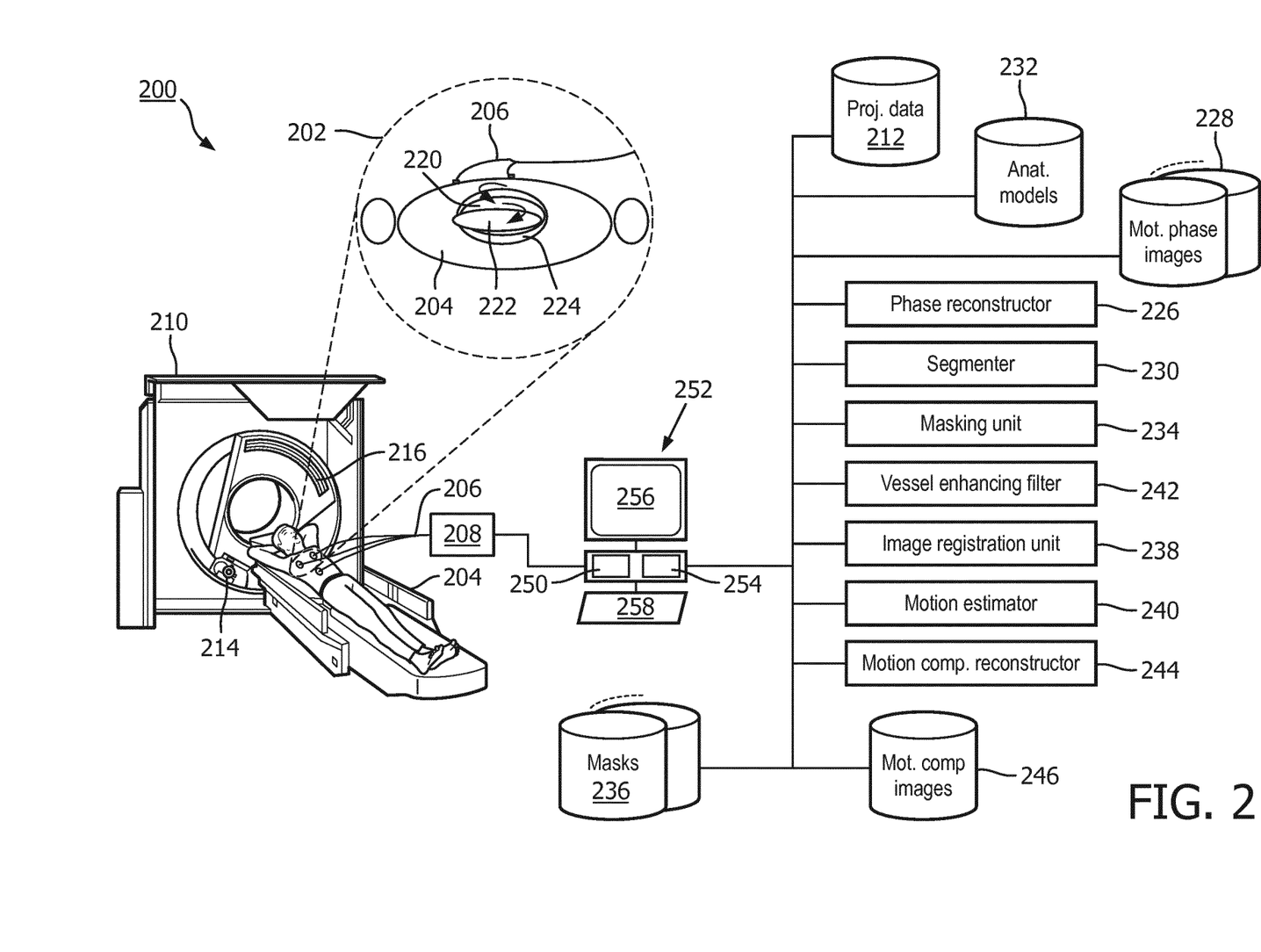
FIG. 2 diagrammatically illustrates an embodiment of a medical imaging system with model regularized motion compensated reconstruction and an exploded cross section view of an examination region.

With reference to FIG. 2, an embodiment of medical imaging system 200 with a model regularized motion compensated reconstruction system. FIG. 2 shows an exploded cross section view 202 of an examination region. A subject 204 is illustrated with metal objects 206, such as electrodes and wire leads of an ECG monitoring device 208.

A medical imaging scanner, such as a CT scanner 210, acquires projection data 212 of the portion of the subject 204 in the examination region. The CT scanner 210 includes an X-ray radiation source 214 that rotates around the subject 204 in the examination region. The X-ray radiation source 214 emits X-ray radiation that traverses the portion of the subject 204 in the examination region and is detected by detectors 216 that generate the projection data 212. The projection data 212 includes the metal objects 206 also present in the examination region, such as electrodes, wire leads, sutures, staples, sternal wires, and the like or combinations thereof.

The CT scanner 210 is configured to acquire projection data 212 at a target motion phase of an anatomical structure 220, such as a heart and/or a lung, and a plurality of temporal neighboring motion phases 222, 224, such as a prior motion phase and a subsequent motion phase. An example of gated reconstruction can be found in "GATED IMAGE RECONSTRUCTION" published as WO/2010/073147 on Jan. 7, 2010. A target phase can be indicated relative to r-waves, such as 40%, 50% and the like. In one embodiment, the projection data 212 is acquired within a single rotation of the source 214 around the subject 204, that is, 240° or greater. In some instances, acquiring the projection data 212 within a single rotation minimizes the radiation exposure by the subject 204. The projection data 212 can be gated retrospectively or prospectively. For example, the projection data 212 can be time stamped and stored with corresponding motion sensor measurements and portions of the projection data 212 corresponding to target and temporal neighboring phases retrospectively selected for reconstruction. In another example, the projection data 212 can be prospectively limited and binned according to target and temporal neighboring phases.

A phase reconstructor 226 reconstructs motion phase images 228 from the projection data 212. The motion phase images 228 are volumetric images, each according to a corresponding motion phase. The motion phase images 228 include a target phase image and a plurality of temporal neighboring phase images.

A segmenter 230 segments one or more anatomical structures in each of the motion phase images 228 and fits a corresponding anatomical model 232 to the segmented anatomical structure. For example, a heart is segmented in the target phase image according to a heart model, and lungs are segmented according to a lung model. In another example, a visceral cavity is segmented according to a visceral cavity model. The model 232 includes surfaces corresponding to external surfaces of the anatomical structure. For example, a mesh model is fit to external surfaces of the segmented heart. The model 232 provides a deformable or elastic surface.

A masking unit 234 constructs a volumetric mask 236 for each reconstructed volumetric phase image that masks portions of the corresponding image external to the segmented anatomical structure 220, 222, 224 and/or fitted model. The masking unit 234 can dilate the mask a predetermined distance from the segmented at least one anatomical structure. In some instances, the masked images mask or remove the portion of the images affected by streak artifacts due to the metal objects 206.

An image registration unit 238 registers the masked reconstructed volumetric phase images. A suitable example of elastic registration of images can be found in "Elastic Image Registration" U.S. Pat. No. 8,326,086. In one embodiment, the registration includes elastic registration with deformable mappings between the fitted model of each masked reconstructed volumetric phase image. In another embodiment, the registration includes elastic registration with deformable mappings between the segmented anatomical structures of each masked reconstructed volumetric phase image. The mappings can be represented as a transformation matrix, motion field vectors, and the like.

A motion estimator 240 estimates motion between each of the registered masked reconstructed volumetric phase images according to the model. The motion can be rigid and/or non-rigid motion. In some instances, the motion estimates excludes apparent motion due to streak artifacts from non-moving metal objects 206. For example, the motion estimator 240 estimates motion field vectors according to each motion phase.

In one embodiment, a vessel enhancing filter 242 enhances vascular structures in the reconstructed volumetric phase images 212. In one embodiment, the vessel enhancing filter 242 enhances vascular structures in the masked reconstructed volumetric phase images. Combinations are contemplated. The vessel enhancing filter 242 can be implemented using vessel enhancing techniques known in the art, such as edge enhancements.

A motion compensating reconstructor 244 reconstructs a motion compensated CT image 246, such as a motion compensated cardiac CT image, from the CT projection data 212 using the estimated motion of the registered masked reconstructed volumetric phase images. A suitable example of motion compensated reconstruction can be found in "Motion compensated CT reconstruction of high contrast objects" U.S. Pat. No. 8,184,883. The reconstructed motion compensated CT image 246 can be displayed on a display device 256 and/or stored in a storage subsystem, such as a Picture Archiving and Communication System (PACS), departmental radiology information system (RIS), electronic medical record (EMR), and the like.

The phase reconstructor 226, the segmenter 230, the masking unit 234, the image registration unit 238, the motion estimator 240, the vessel enhancing filter 242 and the motion compensated reconstructor 244 are suitably embodied by one or more configured processors, such as one or more processors 250 of a computing device 252. The configured processor(s) 250 executes at least one computer readable instruction stored in computer readable storage medium, such as the memory 254 of the computing device 252, which excludes transitory medium and includes physical memory and/or other non-transitory medium to perform the disclosed phase reconstruction, segmentation, mask construction, vessel enhancement, registration, motion estimation, and motion compensated reconstruction techniques. The configured processor may also execute one or more computer readable instructions carried by a carrier wave, a signal or other transitory medium. The computing device 252 can comprise a workstation, laptop, tablet, smart phone, body worn computing device, server, and the like. The lines between components represented in the diagram represent communications paths, which can be wired or wireless.

The computing device 252 includes the display device 256, such as a computer display, projector, body worn display, and the like, and one or more input devices 258, such as a mouse, keyboard, microphone, touch or gesture interface, and the like. The computing device 252 includes the one or more processors 250, such as a digital processor, a microprocessor, an electronic processor, an optical processor, a multi-processor, a distribution of processors including peer-to-peer or cooperatively operating processors, client-server arrangement of processors, and the like.

Figure 3:
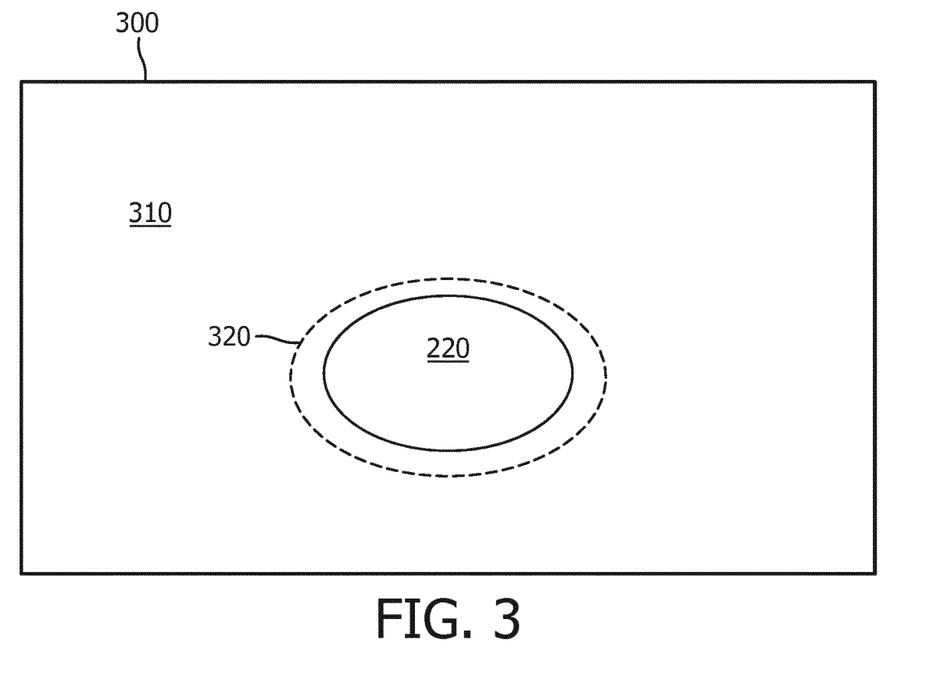
FIG. 3 diagrammatically illustrates an embodiment of masked reconstructed motion phase image.

With reference to FIG. 3, an embodiment of masked reconstructed motion phase image 300 is diagrammatically illustrated. The masked reconstructed motion phase image 300 is constructed from a reconstructed motion phase volumetric image 228. The masked reconstructed motion phase image 300 includes the segmented anatomical structure 220 according to a fitted anatomical model. For example, in a cardiac phase image at a selected phase, the image includes the heart with portions of the image external to the heart masked. The masked portions 310 of the image can include images values set to zero Hounsfield Units (HU), null values or the like.

Dilating the mask includes a margin 320 around the segmented structure and/or anatomical model, which is not masked. For example, using orthogonal projections from the surface of the model a margin of 2.5 pixels, the unmasked portion includes the heart and the margin around the surface of the heart of 2.5 pixels. In some instances, using the masked images isolates the registration and computed motion estimated to actual deformable motion of the heart and/or lungs, while permitting existing image registration algorithms, and motion computations.

Figure 4:
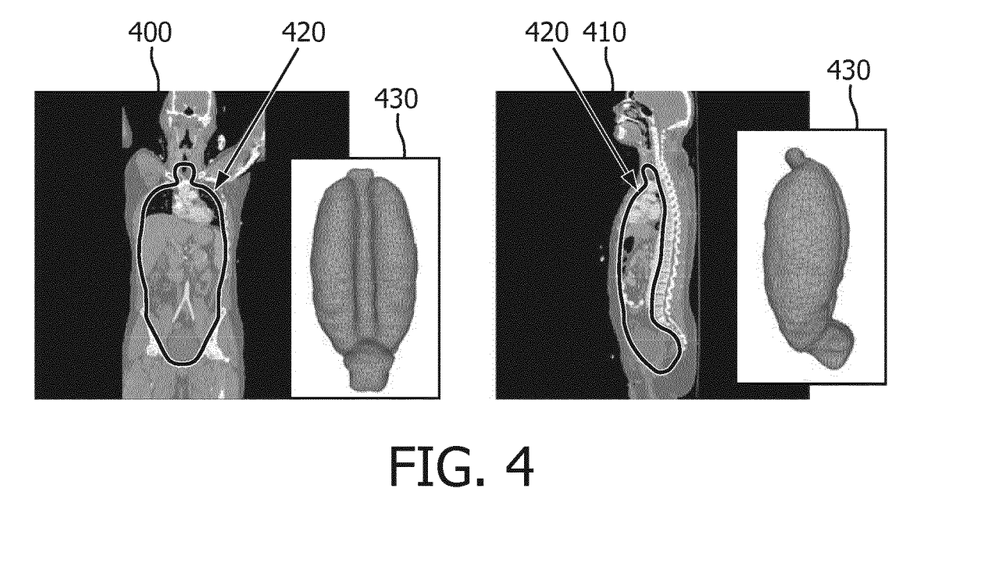
FIG. 4 illustrates an example in a frontal view and a side view of a visceral cavity model fitted in an image of a subject and the corresponding visceral cavity model in a separate view.

With reference to FIG. 4, an example in a front view 400 and a side view 410 of a visceral cavity model 420 fitted in an image cross section of a subject and the corresponding visceral model in a separate view 430 is illustrated. The visceral cavity model 420 includes a mesh surface model confining inner organs of a subject, such as lungs, a liver, a heart, a colon, a stomach, a prostate, and the like, while excluding surrounding tissues of muscle, fat and bones, such as ribs, vertebrae, pelvic bone, hips, and the like. The visceral cavity model 420 fitted to the anatomy of the subject constrains or regularizes the motion by motion estimated according to the masked registrations, that is, limited to the volume of the fitted model or dilated fitted model.

Figure 5:
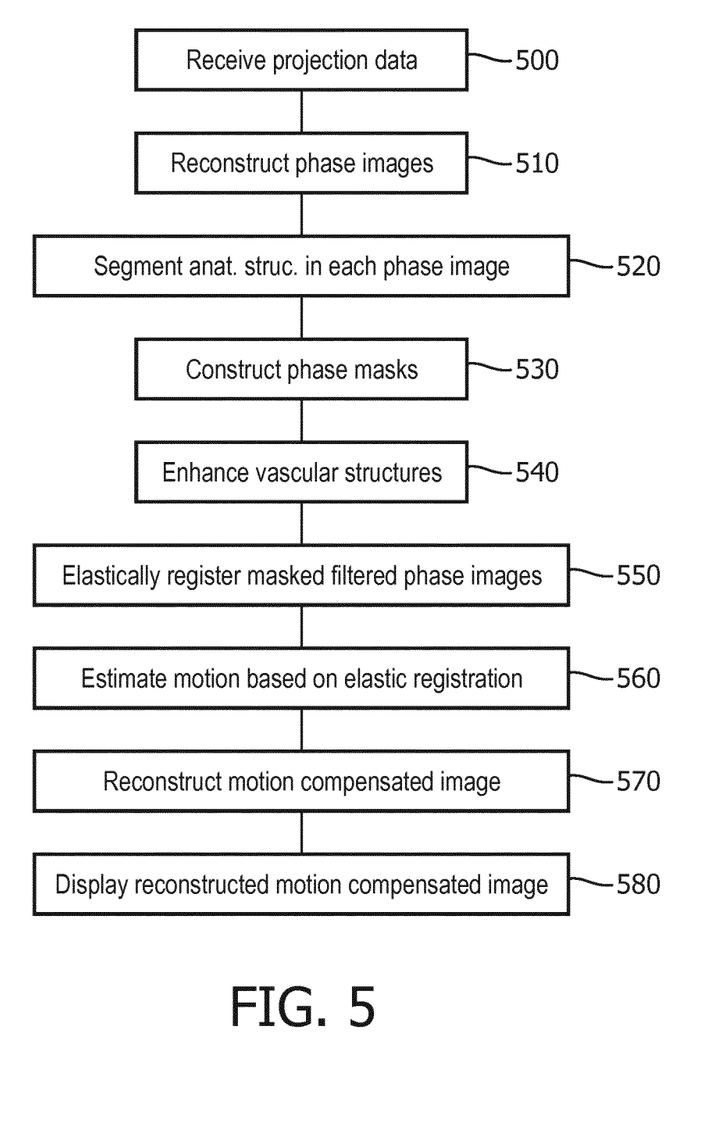
FIG. 5 flowcharts an embodiment of a method of model regularized motion compensated medical image reconstruction.

With reference to FIG. 5, an embodiment of a method of model regularized motion compensated CT reconstruction is flowcharted. At 500, projection data 212 is received. The projection data 212 can be received directly from the CT scanner 210. The projection data 212 can be received from a storage subsystem, such as the PACS, RIS, EMS, and the like.

At 510, volumetric phase images 228 are reconstructed from the projection data 212. The volumetric phase images 228 include a target motion phase and a plurality of temporal neighboring motion phases of an anatomical structure, such as a heart, lung, combinations and the like.

At 520 the anatomical structure(s) in each of the reconstructed volumetric phase images are segmented and an anatomical model is fitted to each segmented anatomical structure. For example, a heart is segmented and a heart model fitted to the segmented heart, the lungs are segmented and a lung model is fitted to the segmented lungs, a visceral cavity is segmented and a visceral cavity model is fitted to the segmented visceral cavity. The models include surfaces that correspond to the external surfaces of the anatomical structure.

A volumetric mask is constructed for each reconstructed volumetric phase image that masks portions of the corresponding image external to the segmented anatomical structure at 530. The volumetric mask can be dilated a predetermined distances from the segmented anatomical structure and/or model. For example, the mask portion of each reconstructed volumetric phase image includes the portions external to the segmented anatomical structure with a margin of a predetermined distance from the external surfaces according to the segmented structure and/or anatomical model.

At 540, vascular structures can be enhanced with a vessel enhancing filter 242. The vascular structures can be enhanced with a filter that provides greater intensity and/or contrast to vascular structures, such as the coronary artery vessel tree. The enhancement can be performed to the reconstructed motion phase images, and/or the masked reconstructed motion phase images.

At 550 the masked reconstructed volumetric phase images are registered, such as an elastic registration.

At 560 motion is estimated between the motion phases according to the model based on the registered masked reconstructed volumetric phase images. In one embodiment, the registration is to the target phase. In another embodiment, the registration includes registration between each phase and every other phase.

At 570 a motion compensated CT image is reconstructed from the CT projection data 212 using the estimated motion of the registered masked reconstructed volumetric phase images.

At 580, the motion compensated CT image is displayed on a display device 256 and/or stored in a storage subsystem.

The above may be implemented by way of computer readable instructions, encoded or embedded on computer readable storage medium, which, when executed by a computer processor(s), cause the processor(s) to carry out the described acts. Additionally or alternatively, at least one of the computer readable instructions is carried by a signal, carrier wave or other transitory medium.

In another embodiment, after the motion compensated reconstruction, the segmented structure is cut out and pasted into a non-motion compensated image replacing the non-motion compensated anatomical structure. In another embodiment, in estimating the motion, the motion vector fields outside the anatomical structure are set to zero with a smooth transition to the zero vector field external to the surfaces of the anatomical structure. In another embodiment, in estimating the motion, the motion vectors fields around the metal object and external to the anatomical structure can be set to zero. The spatial locations of the metal object can be identified based on high HU values. In some instances, setting the motion vectors to zero around the metal object can avoid a misregistration of the anatomical structure.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. A medical imaging system, comprising:
   a memory that stores a plurality of instructions; and
   processor circuitry that couples to the memory and is configured to execute the plurality of instructions to:
   construct a mask for each reconstructed volumetric phase image of a plurality of reconstructed volumetric phase images that masks portions of a corresponding image external to an anatomical model fitted to a segmented at least one anatomical structure, wherein the plurality of reconstructed volumetric phase images include a target phase and a plurality of temporal neighboring phases reconstructed from projection data;
   register the masked reconstructed volumetric phase images;
   estimate motion between the target phase and the plurality of temporal neighboring phases according to the anatomical model based on the registered masked reconstructed volumetric phase images; and
   reconstruct a motion compensated medical image from the projection data using the estimated motion of the registered masked reconstructed volumetric phase images.

2. The system according to claim 1, wherein the processor circuitry is further configured to dilate the mask a predetermined distance from the segmented at least one anatomical structure.

3. The system according to claim 1, wherein the processor circuitry is further configured to enhance vascular structures in the reconstructed volumetric phase images.

4. The system according to claim 1, wherein the projection data includes computed tomography (CT) projection data.

5. The system according to claim 1, wherein the at least one anatomical structure includes at least one of a heart, a lung and a visceral cavity.

6. The system according to claim 1, wherein the anatomical model includes at least one of an anatomical heart model, an anatomical lung model and a visceral cavity anatomical model.

7. The system according to claim 6, wherein the visceral cavity model includes a surface that encloses inner organs of a subject and excludes bones and surrounding tissues.

8. The system according to claim 1, further including:
   a CT scanner configured to acquire the projection data within a single rotation of an x-ray radiation source about a subject.

9. The system according to claim 1, wherein the projection data includes a subject and metallic objects.

10. The system according to claim 9, wherein the metallic objects include at least one of electrodes, wire leads, sutures, staples, sternal wires and combinations thereof.

11. A method of motion compensated medical image reconstruction, comprising:
    constructing a mask for each reconstructed volumetric phase image of a plurality of reconstructed volumetric phase images that masks portions of a corresponding image external to an anatomical model fitted to a segmented at least one anatomical structure, wherein the plurality of reconstructed volumetric phase images include a target phase and a plurality of temporal neighboring phases reconstructed from projection data;
    registering the masked reconstructed volumetric phase images;
    estimating motion between the target phase and the plurality of temporal neighboring phases according to the anatomical model based on the registered masked reconstructed volumetric phase images; and
    reconstructing a motion compensated medical image from the projection data using the estimated motion of the registered masked reconstructed volumetric phase images.

12. The method according to claim 11, wherein constructing includes:
    dilating the mask a predetermined distance from the segmented at least one anatomical structure.

13. The method according to claim 11,
    enhancing vascular structures with a filter in at least one of:
    the reconstructed volumetric phase images; and
    the masked reconstructed volumetric phase images.

14. The method according to claim 11, wherein the at least one anatomical structure includes at least one of a heart, a lung and a visceral cavity.

15. The method according to claim 11, further including: acquiring the projection data within a single rotation of an x-ray radiation source of a CT scanner about a subject.

16. The method according to claim 11, wherein the projection data includes a subject and metallic objects.

17. The method according to claim 16, wherein the metallic objects include at least one of electrodes, wire leads, sutures, staples, sternal wires and combinations thereof.

18. A non-transitory computer-readable storage medium carrying software which controls one or more processors to perform the method according to claim 11.

19. A processor configured to perform the method according to claim 11.

20. A method of motion compensated computed tomography (CT) reconstruction, comprising:
   reconstructing volumetric phase images at a target phase and a plurality of temporal neighboring phases of at least one anatomical structure of a subject from CT projection data;
   segmenting the at least one anatomical structure in each of the reconstructed volumetric phase images using a model based segmentation that fits the model to the at least one anatomical structure;
   constructing a mask for each reconstructed volumetric phase image that masks portions of the corresponding image external a predetermined distance to the surface of the fitted model;
   filtering each masked reconstructed volumetric phase image, which enhances vascular structures in the non-masked regions;
   elastically registering the masked reconstructed volumetric phase images;
   estimating motion between the target phase and the plurality of temporal neighboring phases according to the fitted model based on the elastically registered masked reconstructed volumetric phase images; and
   reconstructing a motion compensated CT image at the target phase from the CT projection data using the estimated motion of the elastically registered masked reconstructed volumetric phase images.

* * * * *